United States Patent
Peery et al.

(10) Patent No.: US 7,163,688 B2
(45) Date of Patent: Jan. 16, 2007

(54) OSMOTIC IMPLANT WITH MEMBRANE AND MEMBRANE RETENTION MEANS

(75) Inventors: John R. Peery, Stanford, CA (US); Scott J. Gilbert, Menlo Park, CA (US); James E. Brown, Los Gatos, CA (US)

(73) Assignee: ALZA Corporation, Mountain View, CA (US)

( * ) Notice: Subject to any disclaimer, the term of this patent is extended or adjusted under 35 U.S.C. 154(b) by 194 days.

(21) Appl. No.: 10/173,992

(22) Filed: Jun. 18, 2002

(65) Prior Publication Data

US 2003/0108590 A1  Jun. 12, 2003

Related U.S. Application Data

(60) Provisional application No. 60/300,575, filed on Jun. 22, 2001.

(51) Int. Cl.
- *A61F 13/00* (2006.01)
- *A61F 2/00* (2006.01)
- *A61K 9/48* (2006.01)

(52) U.S. Cl. .............. 424/422; 424/424; 424/425; 424/451; 424/454

(58) Field of Classification Search ............ 424/422, 424/423, 424, 426
See application file for complete search history.

(56) References Cited

U.S. PATENT DOCUMENTS

| | | | |
|---|---|---|---|
| 3,732,865 A * | 5/1973 | Higuchi et al. | 604/892.1 |
| 3,987,790 A | 10/1976 | Eckenhoff et al. | |
| 4,865,845 A | 9/1989 | Eckenhoff et al. | |
| 5,059,423 A | 10/1991 | Magruder et al. | |
| 5,112,614 A | 5/1992 | Magruder et al. | |
| 5,137,727 A | 8/1992 | Eckenhoff | |
| 5,213,809 A | 5/1993 | Wright et al. | |
| 5,234,692 A | 8/1993 | Magruder et al. | |

(Continued)

FOREIGN PATENT DOCUMENTS

WO    WO 99/33446    7/1999

(Continued)

OTHER PUBLICATIONS

Author unknown, "Engineer's Guide to Plastics," Materials Engineering, Unknown, vol. 5 (No. 72), p. 38-45, (Jul. 17, 1972).

(Continued)

*Primary Examiner*—S. Tran (57) ABSTRACT

An osmotic delivery system for controlled delivery of a beneficial agent includes an implantable capsule containing a beneficial agent and an osmotic engine that swells on contact with water, thereby causing the release of the beneficial agent over time. The osmotic delivery system has a membrane material that allows a controlled amount of fluid to enter from an exterior of the capsule, while preventing the compositions within the capsule from passing out of the capsule. The osmotic delivery system is designed to meet at least the operating pressures of 1000 psi. The membrane material is cast, calendered or extruded followed by machining (i.e., die-cutting, stamping or otherwise cutting to shape) to provide a uniform nonribbed membrane material. The capsule also includes a membrane material-retaining means that is positioned at a fluid uptake end to retain the membrane material within the capsule, even under periods of high pressure.

25 Claims, 5 Drawing Sheets

U.S. PATENT DOCUMENTS

| | | |
|---|---|---|
| 5,234,693 A | 8/1993 | Magruder et al. |
| 5,308,348 A | 5/1994 | Balaban et al. |
| 5,413,572 A | 5/1995 | Wong et al. |
| 5,540,665 A | 7/1996 | Mercado et al. |
| 5,728,396 A | 3/1998 | Peery et al. |
| 5,985,305 A | 11/1999 | Peery et al. |
| 5,997,527 A * | 12/1999 | Gumucio et al. ........ 604/892.1 |
| 6,113,938 A * | 9/2000 | Chen et al. ................ 424/423 |
| 6,287,295 B1 * | 9/2001 | Chen et al. .............. 604/892.1 |
| 6,544,252 B1 * | 4/2003 | Theeuwes et al. ....... 604/892.1 |
| 2003/0114837 A1 * | 6/2003 | Peterson et al. ......... 604/892.1 |
| 2004/0097906 A1 * | 5/2004 | Fereira et al. ............ 604/892.1 |
| 2004/0102762 A1 * | 5/2004 | Gilbert .................... 604/892.1 |
| 2005/0101943 A1 * | 5/2005 | Ayer et al. ............... 604/892.1 |
| 2005/0131389 A1 * | 6/2005 | Peterson et al. ......... 604/892.1 |

FOREIGN PATENT DOCUMENTS

WO     WO 99/33446 A1 *   7/1999

OTHER PUBLICATIONS

Kildsig, D.O. et al., "Theoretical Justification of Reciprocal . . . ," Jrl. Pharma. Sciences, vol. 59 (No. 11), p. 1634-1637, (Nov. 17, 1970).

Rogers, C.E. et al., "Permeability Valves," Ind. and Eng. Chem., vol. 49 (No. 11), p. 1933-1936, (Nov. 17, 1957).

Ann. Book of ASTM Stds., vol. 8.02, pp. 208-211 and pp. 584-587 (1984).

Morgan, P.W.., "Structure and Moisture Permeability . . . ," Ind. Eng. Chem., vol. 45 (No. 10), pp. 2296-2306 (1953).

* cited by examiner

OSMOTIC IMPLANT WITH MEMBRANE AND MEMBRANE RETENTION MEANS

This application claims the priority of U.S. Application Ser. No. 60/300,575 filed Jun. 22, 2001, which is incorporated herein by reference.

BACKGROUND OF THE INVENTION

1. Field of the Invention

The present invention relates to osmotically controlled implantable delivery devices, and more particularly to a delivery system having a membrane material that controls the delivery rate of a beneficial agent from the delivery system, in which the membrane material is cast, calendered or extruded, then machined (i.e., stamped, die cut or otherwise cut to shape), and the membrane material is maintained within the delivery device by a retaining means.

2. Description of the Related Art

Controlled delivery of beneficial agents, such as drugs, in the medical and veterinary fields, has been accomplished by a variety of methods, including implantable delivery devices such as implantable osmotic delivery devices and implantable diffusion controlled delivery systems. Osmotic delivery systems are very reliable in delivering a beneficial agent over an extended period of time called an administration period. In general, osmotic delivery systems operate by imbibing fluid from an outside environment and releasing corresponding amounts of beneficial agent from the delivery system.

Representative examples of various types of delivery devices are disclosed in U.S. Pat. Nos. 3,732,865; 3,987,790; 4,865,845; 5,059,423; 5,112,614; 5,137,727; 5,213,809; 5,234,692; 5,234,693; 5,308,348; 5,413,572; 5,540,665; 5,728,396; and 5,985,305, all of which are incorporated herein by reference. All of the above-cited patents generally include some type of capsule having at least a portion of a wall that selectively passes water into the interior of the capsule containing a water-attracting agent (also called an osmotic agent, an osmopolymer or osmoagent). The absorption of water by the water-attracting agent within the capsule reservoir creates an osmotic pressure within the capsule which causes a beneficial agent within the capsule to be delivered. The water-attracting agent may be the beneficial agent being delivered to the patient. However, in most cases, a separate agent is used specifically for its ability to draw water into the capsule.

When a separate osmotic agent is used, the osmotic agent may be separated from the beneficial agent within the capsule by a movable dividing member, such as a piston. The structure of the capsule is generally rigid such that as the osmotic agent takes in water and expands, the capsule does not expand. As the osmotic agent expands, the agent causes the movable dividing member to move, discharging the beneficial agent through an orifice or exit passage of the capsule. The beneficial agent is discharged through the exit passage at the same volumetric rate that water enters the osmotic agent through the semipermeable wall portion of the capsule.

The rate at which the beneficial agent is discharged from the delivery device is determined by many factors, including the type of water-attracting agent or osmotic agent, the permeability of the semipermeable membrane wall, and the size and shape of the exit passage. One manner in which the back diffusion of environmental fluid into the beneficial agent reservoir is controlled is by a flow moderator in the exit passage of the capsule, with the flow moderator generally consisting of a tubular passage having a particular cross-sectional area and length.

In known osmotic delivery systems, an osmotic tablet, such as salt, is placed inside the capsule and a membrane plug is placed in an open end of the capsule to provide a semipermeable barrier. The membrane plug seals the interior of the capsule from the exterior environment, permitting only certain liquid molecules from the environment to permeate through the membrane plug and into the interior of the capsule. The membrane plug is impermeable to items within the capsule including the osmotic agent and the beneficial agent. The rate at which the liquid permeates the membrane plug and enters the capsule varies depending upon the type of membrane material and the size and shape of the membrane plug. Further, the rate at which the liquid passes through the membrane plug controls the rate at which the osmotic agent expands to thereby drive the beneficial agent from the delivery system through the exit passage. Accordingly, the rate of delivery of the beneficial agent from the osmotic delivery system is controllable by varying the permeability coefficient of the membrane plug and/or the size of the membrane plug.

Some known osmotic delivery systems use injection molded membrane plugs featuring protruding circumferential sealing ribs that fit into matching circumferential grooves on the inside of the capsule (U.S. Pat. No. 6,113,938, which is incorporated herein by reference). The membrane plug is retained in the capsule by the sealing ribs, which usually requires the membrane to be inserted from the membrane end of the reservoir. Injection molded semipermeable membranes may be difficult to manufacture without internal stresses; thus performance may vary slightly from plug to plug. An additional drawback of known osmotic delivery systems is that the membrane plug itself is required to withstand the pressures created by the expansion of the osmotic engine. Other known osmotic delivery systems use membrane plugs with protruding circumferential sealing ribs but no matching circumferential grooves inside of the capsule. Still other known osmotic delivery systems use membrane plugs with no circumferential sealing ribs that fit into the capsule by friction fit. Still other known osmotic delivery systems use membrane plugs without any circumferential sealing ribs but with holes in the capsule into which the membrane plug can expand (WO99/33446, which is incorporated herein by reference). Known delivery systems preclude the use of a capsule having a pre-installed retaining feature covering or partially covering the membrane plug end of the capsule for keeping the membrane plug sealed in position. Consequently, in these systems, if a retaining feature other than the capsule grooves and matching ribs of the membrane plug is to be used, it must be assembled to the main capsule body, after the membrane plug is inserted. This requirement tends to increase the cost and complexity of a high pressure osmotic delivery system.

Accordingly, it is desirable to provide a delivery device that provides improved consistency and performance of the membrane material and also provides a feature for retaining the membrane material within the capsule under high pressure.

SUMMARY OF THE INVENTION

In accordance with the present invention, a delivery system for controlled delivery of a beneficial agent includes an implantable capsule having a beneficial agent delivery end and a fluid uptake end. The capsule also includes a beneficial agent reservoir positioned within the capsule for housing the beneficial agent. A membrane material is received in the fluid uptake end of the capsule and provides a fluid permeable barrier between an interior and an exterior of the capsule. A membrane material-retaining means is positioned at the fluid uptake end of the capsule and includes at least one opening for allowing passage of fluid. The membrane material-retaining means also prevents the membrane material from being ejected out of the fluid uptake end of the capsule.

In another aspect, the present invention is directed to a delivery system for controlled delivery of a beneficial agent in which the membrane material-retaining means includes a retention flange positioned along a proximal end of the fluid uptake end of the capsule.

In accordance with another aspect, the present invention pertains to a delivery system, in which the membrane material-retaining means includes a screen, a grate, a perforated disk, a frit, or a sintered powdered metal structure including porous capillaries. If the membrane material-retaining means includes porous capillaries, the capillaries can have diameters between about 0.5 and about 10 microns. The membrane material-retaining means can be flat or have a rounded or contoured surface on at least one surface thereof.

In a further aspect, the present invention pertains to a delivery system for controlled delivery of a beneficial agent, in which the membrane material has a generally smooth, cylindrical or disc shape.

In yet another aspect, the present invention is directed to a delivery system for controlled delivery of a beneficial agent, in which the membrane material is extruded, cast, or calendered and then machined (i.e., die-cut, stamped, or otherwise cut into shape).

In another aspect, the present invention pertains to a delivery system for controlled delivery of a beneficial agent, in which the capsule includes one or a plurality of inward protruding ridges and in which the inward protruding ridges securely grip an outer surface of the membrane material. Note that the word "ridges" as used herein can indicate one or more ridges. Additionally, the inwardly protruding ridge or plurality of inwardly protruding ridges are shaped to accommodate insertion of the membrane material from the beneficial agent delivery end of the capsule while inhibiting withdrawal of the membrane material from the beneficial agent delivery end of the capsule.

In a further aspect, the present invention is directed to a delivery system for controlled delivery of a beneficial agent, in which an osmotic engine is positioned between the beneficial agent delivery end and the membrane material.

In a further aspect, the present invention pertains to a delivery system for controlled delivery of a beneficial agent and includes a piston positioned between the beneficial delivery end and the osmotic engine for transmitting a pushing force created by the osmotic engine to the beneficial agent.

According to a further aspect of the present invention, a method of forming a beneficial agent delivery device includes the steps of providing an implantable capsule having an open delivery end, an open fluid uptake end and a membrane material-retaining means. A membrane material is inserted into the capsule from the open agent delivery end and positioned such that an end surface thereof is in contact with an inside surface of the membrane material-retaining means. The osmotic agent is inserted into the capsule, followed by a movable dividing means or piston. The capsule is then filled with a beneficial agent, and the agent delivery end is closed while providing a controlled outlet for the beneficial agent to escape when sufficient pressure is applied to the beneficial agent.

In a further aspect, the present invention pertains to an osmotic system for controlled delivery of a beneficial agent including an implantable capsule having a beneficial agent delivery end and a fluid uptake end. The capsule includes a beneficial agent reservoir positioned adjacent the beneficial agent delivery end for housing the beneficial agent. A piston is positioned between the beneficial agent reservoir and the fluid uptake end. An osmotic engine is positioned between the piston and the fluid uptake end. The osmotic engine is expandable at a controlled rate and when expanding, applies a pushing force against the piston which applies a pushing force against the beneficial agent, such that the beneficial agent is released through the beneficial agent delivery end at a predetermined rate. A membrane material is received in the fluid uptake end and provides a fluid permeable barrier between an interior and an exterior of the capsule. A membrane material-retaining means is positioned at the fluid uptake end, with the membrane material-retaining means including at least one opening for allowing passage of fluid. The membrane material-retaining means also prevents the membrane material from being ejected out of the fluid uptake end of the capsule by osmotic pressure.

The present invention provides the advantage of consistent and predictable delivery rate of a beneficial agent by allowing the use of extruded, cast, or calendered and then machined (i.e., die cut, stamped or otherwise cut to shape) membrane materials, whose consistency is more homogeneous when produced on a highly controlled machining or extrusion line as compared to the part-to-part consistency of injection molded membrane plugs.

The present invention also provides the advantage of allowing the sealing of a cast, calendered, or extruded membrane material that has been machined (i.e., die cut, stamped or otherwise cut to shape) in place in an implantable osmotic delivery device while reducing the expulsion of the membrane from the implantable device under high pressure conditions (greater than 1,000 psi), such as those encountered in the case of a blocked exit passage.

In addition, the present invention allows for the membrane material-retaining means to be formed integrally with the implantable capsule or attached thereto during assembly of the delivery device.

BRIEF DESCRIPTION OF THE DRAWINGS

The invention will be described in greater detail with reference to the accompanying drawings in which like elements bear like reference numerals, and wherein.

DETAILED DESCRIPTION OF THE INVENTION

The present invention relates to an osmotic delivery system 10 having a membrane material 30 for controlling a delivery rate of a beneficial agent from the osmotic delivery system.

DEFINITIONS

The term "active agent" or "beneficial agent" intends the active agent(s) optionally in combination with pharmaceutically acceptable carriers and optionally additional ingredients such as antioxidants, stabilizing agents, permeation enhancers, etc.

The term "impermeable" intends that the material is sufficiently impermeable to environmental fluids as well as ingredients contained within the dispensing device such that the migration of such materials into or out of the device through the impermeable device is so low as to have substantially no adverse impact on the function of the device during the delivery period.

The term "semipermeable" intends that the material is permeable to external fluids but substantially impermeable to other ingredients contained within the dispensing device and the environment of use.

The term "membrane material" intends that the semipermeable membrane is in the form of a sheet or plug. The membrane material preferably has a diameter between about 0.040 inch and about 0.250 inch and preferably has a length or thickness between about 0.010 inch and about 0.350 inch. The diameter and thickness of the membrane material are determined by such considerations as desired rate of delivery of the beneficial agent, desired duration of delivery of the beneficial agent, the device size, the material used for the semipermeable membrane, the retention means for the semipermeable membrane, the beneficial agent formulation, and/ or the osmotic pressure generated during operation of the device.

Figure 1:
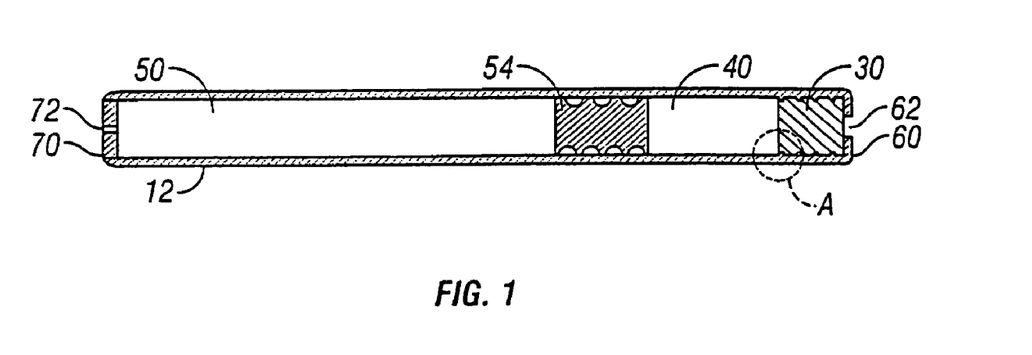
FIG. 1 is a cross-sectional side view of an osmotic drug delivery device including a capsule, a piston, an osmotic engine, a membrane, and an exit passage.

FIG. 1 shows that the osmotic delivery system 10 generally includes a first chamber 50 which contains a beneficial agent, a piston 54 and a second chamber 40 containing an osmotic agent, all of which are enclosed within an elongated substantially cylindrical capsule 12.

The capsule 12 must be sufficiently strong to ensure that it will not leak, crack, break or distort so as to expel its active agent contents under stresses it would be subjected to during use. In particular, it should be designed to withstand the maximum osmotic pressure that could be generated by the osmotic agent in chamber 40. Capsule 12 must also be chemically inert, biocompatible, and impermeable, that is, it must be nonreactive with the active agent formulation as well as the body and must isolate the beneficial agent during the delivery process. Suitable materials generally comprise a nonreactive polymer or a biocompatible metal or alloy. The polymers include acrylonitrile polymers such as acrylonitrile-butadiene-styrene terpolymer, and the like; halogenated polymers such as polytetrafluorethylene, polycholortrifluoro-ethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; polyether ether ketone (PEEK); liquid crystal polymer (LCP); and the like. The water vapor transmission rate through compositions useful for forming the reservoir are reported in *J. Pharm. Sci.*, Vol. 29, pp. 1634–37 (1970); *Ind. Eng. Chem.*, Vol. 45, pp. 2296–2306 (1953); *Materials Engineering*, Vol. 5, pp. 38–45 (1972); *Ann. Book of ASTM Stds.*, Vol. 8.02, pp 208–211 and pp. 584–587 (1984); and *Ind. and Eng. Chem.*, Vol. 49, pp. 1933–1936 (1957). Metallic materials useful in the invention include stainless steel, titanium, platinum, tantalum, gold and their alloys as well as gold-plated ferrous alloys, platinum-plated ferrous alloys, cobalt-chromium alloys and titanium nitride coated stainless steel. A reservoir made from titanium or a titanium alloy having greater than 60%, often greater than 85%, titanium is particularly preferred.

The capsule 12 has a delivery end 70 with an exit passage 72 in it at the beneficial agent delivery end 70 and an opening 62 at the fluid uptake end of the capsule 12. The exit passage 72 may take any convenient form such as straight, circular, spiral, etc. The exit passage 72 is made of an inert and biocompatible material selected from, but not limited to, metals, including, but not limited to, titanium, stainless steel, platinum and their alloys and cobalt-chromium alloys and the like, and polymers, including, but not limited to, polyethylene, polypropylene, polycarbonate and polymethylmethacrylate and the like.

Figure 2:
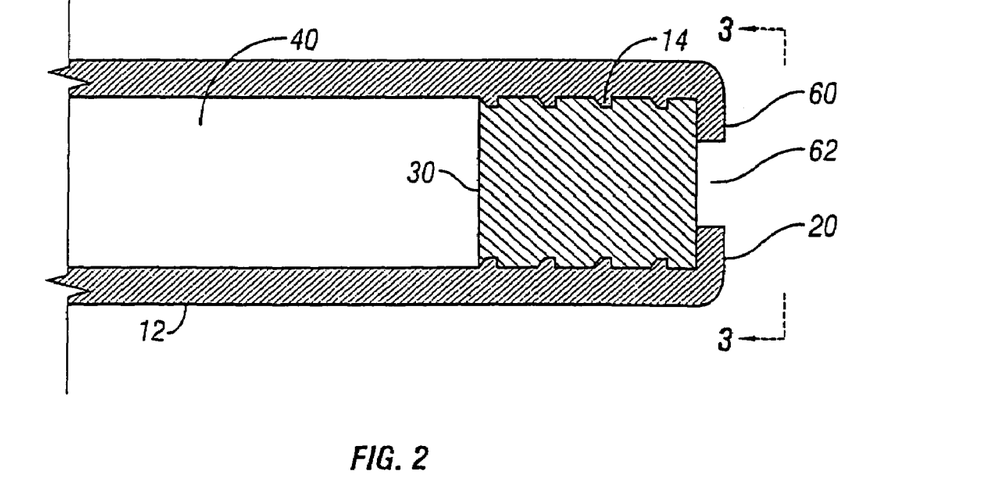
FIG. 2 is a cross-sectional side view of a portion of an implantable capsule.

The fluid uptake end 60 of the capsule 12 is closed by the membrane material 30. In FIG. 2 the membrane material is in the form of a plug. Materials from which the membrane materials are made are those that are semipermeable and that can conform to the shape of the capsule 12 upon wetting and sealing to the rigid surface of the capsule 12. The semipermeable membrane material 30 expands as it hydrates when placed in a fluid environment so that a seal is generated between the mating surfaces of the membrane material and the capsule. The diameter of the membrane material is such that it will sealingly fit inside the reservoir prior to hydration as a result of sealing contact at one or more circumferential or axial zones and will expand in place upon wetting to form an even tighter seal with the capsule. The membrane material must be able to imbibe between about 0.1% and 200% by weight of water. The polymeric materials from which the semipermeable membrane material may be made vary based on the pumping rates and the device configuration requirements and include, but are not limited to, plasticized cellulosic materials, enhanced polymethylmethacrylate such as hydroxyethylmethacrylate (HEMA) and elastomeric materials such as polyurethanes and polyamides, polyetherpolyamide copolymers, thermoplastic copolyesters and the like.

The membrane material 30 closes the fluid uptake end 60 from the second chamber 40 containing the osmotic agent.

The osmotic agent or osmotic engine may include, for example, a nonvolatile water soluble osmoagent, an osmopolymer which swells on contact with water, or a mixture of the two. Osmotic agents, such as NaCl with appropriate tabletting agents (lubricants and binders) and viscosity modifying agents, such as sodium carboxymethylcellulose or sodium polyacrylate are preferred water-swellable agents. Other osmotic agents useful as the water-swellable agent include osmopolymers and osmoagents and are described, for example, in U.S. Pat. No. 5,413,572, which is incorporated by reference herein. The water-swellable agent formulation can be a slurry, a tablet, a molded or extruded material or other form known in the art. A liquid or gel additive or filler may be added to chamber 40 to exclude air from spaces around the osmotic engine.

Fluid passes through the membrane material 30 from an exterior of the capsule 12 and into the second chamber 40, while the membrane material 30 prevents the compositions within the capsule 12 from passing out of the capsule 12.

As seen in FIG. 1, the first chamber 50, containing the beneficial agent, is separated from the second chamber 40, containing the osmotic agent, by a separating member, such as the movable piston 54. The movable piston 54 is a substantially cylindrical member configured to fit within the interior diameter of the capsule 12 in a sealing manner and to slide along a longitudinal axis inside the capsule 12. The piston 54 provides an impermeable barrier between the beneficial agent contained in the first chamber 50 and the osmotic agent contained in the second chamber 40. The materials from which the piston are made are preferably elastomeric materials that are impermeable and include, but are not limited to, polypropylene, rubbers such as EPDM, silicone rubber, butyl rubber, and the like, perfluoro-elastomers, such as Kalrez® and Chemrez®, fluorocarbons such as Viton®, and thermoplastic elastomers such as plasticized polyvinylchloride, polyurethanes, Santoprene®, C-Flex® TPE, a styrene-ethylene-butylene-styrene copolymer (Consolidated Polymer Technologies Inc.), and the like.

Figure 3:
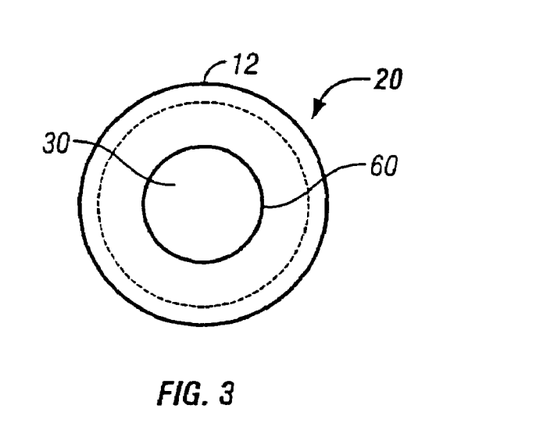
FIG. 3 is a front view along line 3—3 of the implantable capsule of FIG. 2.

As seen in FIGS. 2 and 3, the capsule 12 includes a smooth, generally cylindrical shape having a hollow interior. The capsule 12 is provided with a membrane material-retaining means having a retention flange 20 positioned along an outer periphery of the fluid uptake end 60 and includes an opening 62 to allow for the passage of fluid into the capsule 12. The membrane retention flange 20 can have a flat, rounded, or contoured surface on the exterior side. The retention flange 20 of the membrane material-retaining means should be long enough to retain the membrane material 30 under full osmotic pressure, yet the opening 62 needs to maximize the exposed surface of the membrane material. The capsule 12 also includes one or a plurality of inwardly protruding annular ribs or ridges 14 which provide fluid sealing between the interior surface of the capsule 12 and the outer surface of the membrane material 30 and prevent fluid from leaking around the membrane material. The ribs or ridges 14 are also formed to grippingly engage the outer surface of the membrane material 30 and prevent the membrane material 30 from moving in a lateral direction towards the beneficial agent delivery end 70. In this respect, the diameter of the membrane material 30 is substantially equal to the inner diameter of the capsule 12. Moreover, the diameter of the membrane material 30 is larger than the inner diameter of the ribs or ridges 14. The capsule may be provided with between about 1 to 8 ribs or ridges, but is preferably provided with about 1 to 4 ribs or ridges. Any reference to the word "ribs" is intended to include a single rib as well as a plurality of ribs. Any reference to the words "ridge" or "ridges" is intended to be a reference to the words "rib" or "ribs," and vice versa.

Although FIG. 2 depicts the retention flange 20 as being formed integrally with the capsule 12, it will be understood that the retention flange may alternatively be a separate member attached to the capsule. For example, the membrane retention flange 20 may be welded, pressed, screwed or the like to the end of the capsule 12.

The opening 62 is sufficiently small that the membrane material 30 cannot distort and pass through the opening under high operating pressures, such as about 5000 psi.

Figure 4:
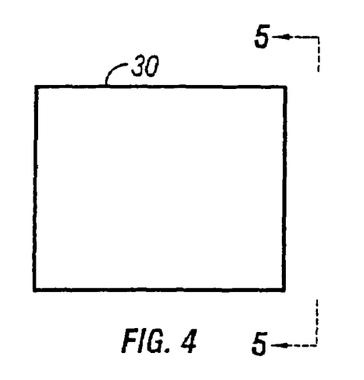
FIG. 4 is a side view of a membrane plug.
Figure 5:
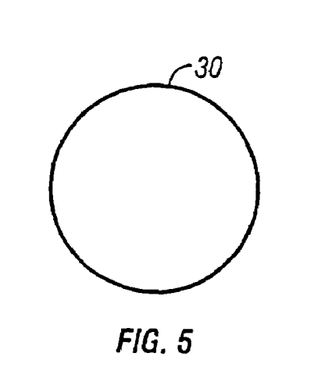
FIG. 5 is a front view along line 5—5 of the membrane plug of FIG. 4.

The membrane material 30, as seen in FIGS. 4 and 5, includes a substantially smooth cylindrical body. As seen in FIGS. 4 and 5, the membrane material 30 is devoid of any protrusions, ribs, or abscesses. Thus, the membrane material 30 is simpler to manufacture than known membrane plugs. The membrane material 30 may be produced by casting, calendering, or extrusion, then machining (i.e., die-cutting, stamping or otherwise cutting to shape), thereby yielding a membrane of superior consistency compared with injection molded membrane materials of known systems. The membrane material 30 may be made of any suitable biocompatible membrane material.

Figure 10:
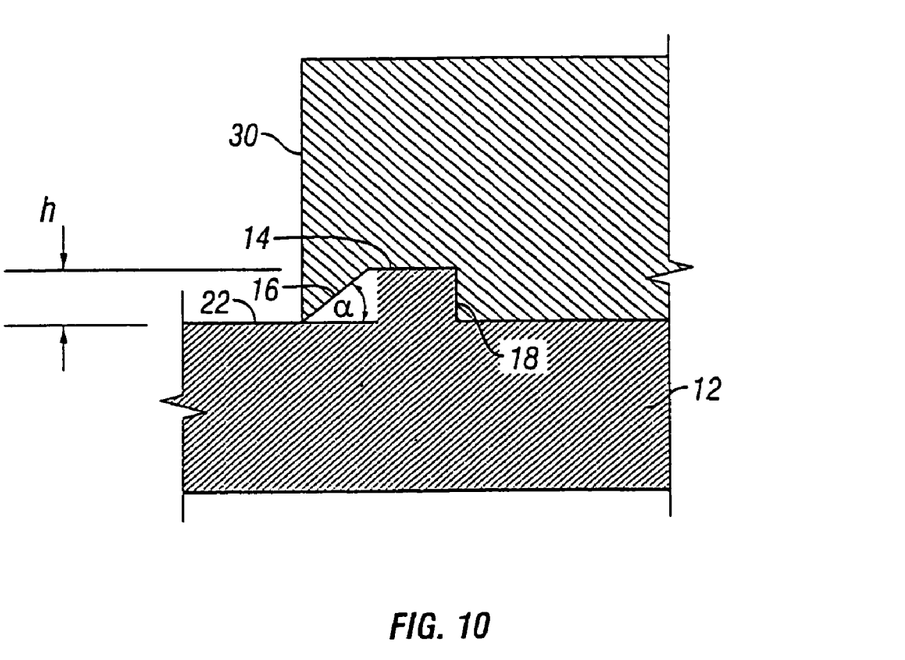
FIG. 10 is an enlarged view of the detail A of FIG. 1.

As seen in FIG. 10, the inwardly protruding ridges 14 include a sloped wall 16 and a vertical wall 18. The ridges 14 extend a distance from the inner wall 22 of the capsule 12, about the entire circumference of the inner wall. The height h of vertical wall 18 preferably is about 0.002" to about 0.020". In addition, the sloped wall 16 is provided at an angle $\alpha$ from the inner wall 22. The angle of the sloped wall 16 can be chosen to be any suitable angle that allows for the membrane material 30 to be easily inserted over the ridges 14. The vertical wall 18 of the ridges 14 prevents the membrane material 30 from moving laterally towards the beneficial agent delivery end 70. In use, the ridges 14 and the membrane retention flange 20 act together to restrict any lateral movement of the membrane material 30.

Although FIG. 10 does not show any clearance between the membrane material 30 and the ridges 14, it is within the scope of the present invention that gaps may exist therebetween and between the inner wall 22 of the capsule 12 and the membrane material 30.

Figure 6:
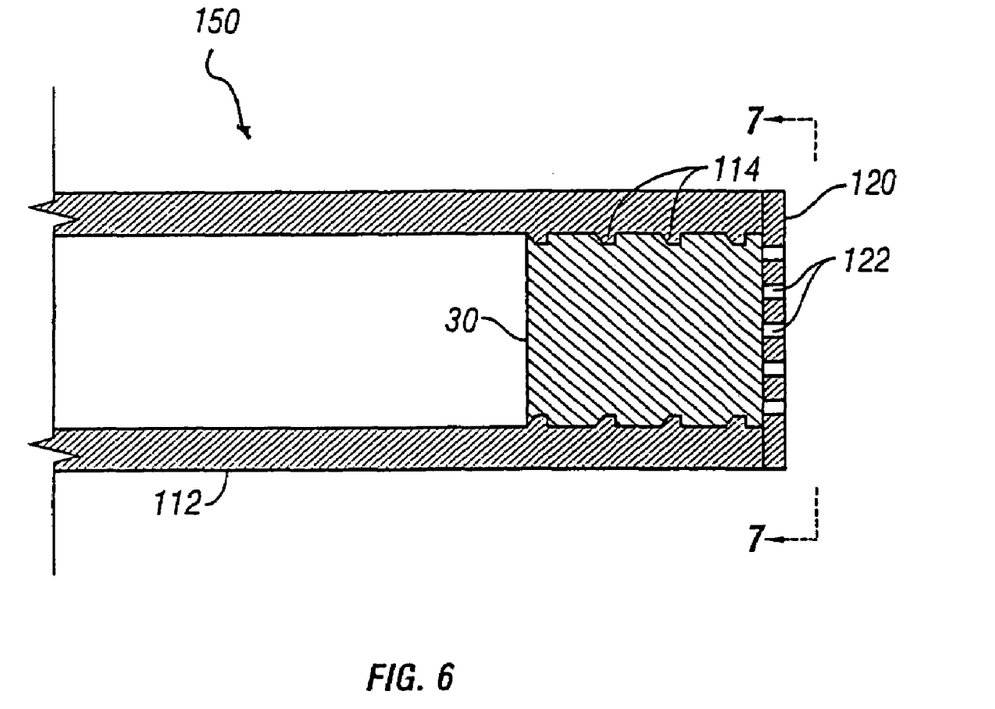
FIG. 6 is a cross-sectional side view of a portion of an implantable capsule according to a second embodiment of the invention.
Figure 7:
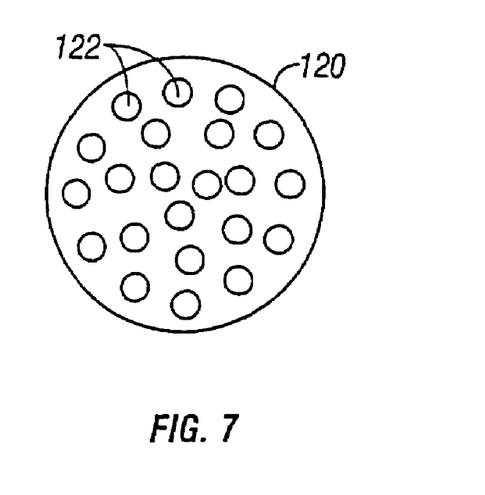
FIG. 7 is a front view taken along line 7—7 of the implantable capsule of FIG. 6.

FIGS. 6 and 7 show a portion of a second preferred embodiment of an osmotic delivery system 150. In this embodiment, the membrane material-retaining means comprises a perforated disk 120. The perforated disk 120 includes a plurality of openings 122 which allow fluid to pass therethrough and subsequently through the membrane material 30 and into the interior of the capsule. As can also be seen in FIG. 6, the perforated disk 120 acts together with the ridges 114 to restrict the lateral movement of the membrane material 30 within the capsule 112. Thus, ridges 114 function in the same manner as the ridges 14 of the first embodiment. In this embodiment, the perforated disk 120 is affixed by welding, pressing, screwing or the like, to the fluid uptake end of the capsule 112.

Figure 8:
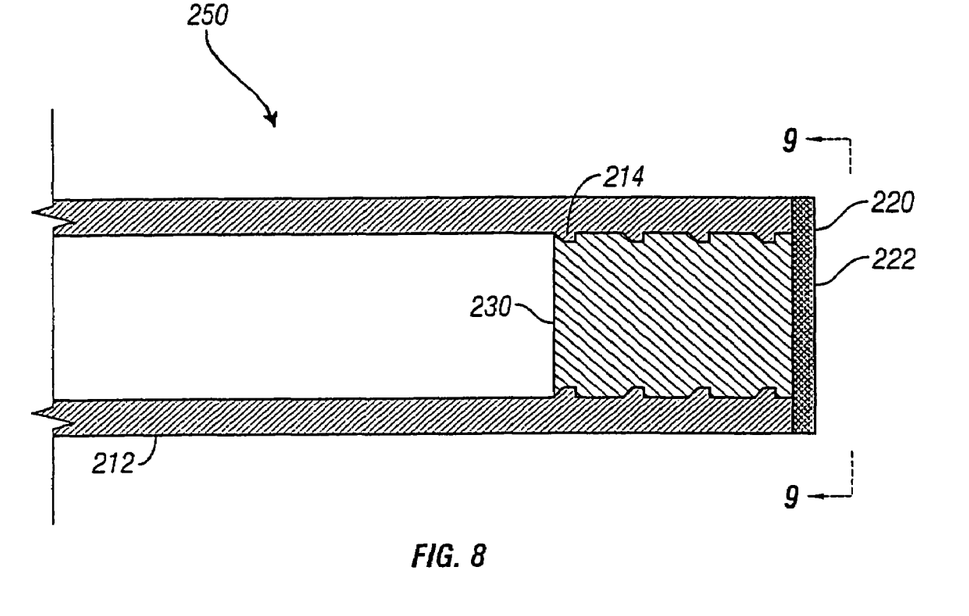
FIG. 8 is a cross-sectional side view of a portion of an implantable capsule according to a third embodiment of the invention.
Figure 9:
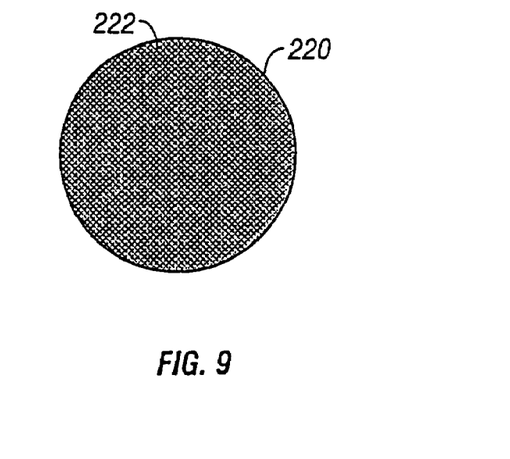
FIG. 9 is a front view taken along line 9—9 of the implantable capsule of FIG. 8.

FIGS. 8 and 9 illustrate a portion of a third preferred embodiment of an osmotic delivery device 250. In this embodiment, a screen or a grate 220 having a plurality of openings 222 is affixed to the fluid uptake end 60 (see FIG. 2) of the capsule 212. As in the previous embodiment, the screen or grate 220 may be welded, pressed, screwed, or otherwise affixed to the fluid uptake end 60 (see FIG. 2) of the capsule 212. The screen or grate 220 may be affixed to the capsule 212 either before or after insertion of the membrane material 230. Although a screen or grate 220 has been illustrated, other structures that allow passage of water and prevent the membrane material 230 from being expelled may also be used.

As also seen in FIG. 8, the capsule 212 is provided with a plurality of inward protruding, circumferentially extending, sealing ribs or ridges 214 having a smaller inner diameter than the inner diameter of the capsule 212. The ridges 214 include sloped walls 16 and vertical walls 18 (see FIG. 10). The sloped walls 16 allow for the easy insertion of the membrane material 230 into the capsule 212 while the vertical walls 18 prevent the transverse movement of the membrane material 230 in the direction of the beneficial agent delivery end 70 (see FIG. 1).

Figure 11:
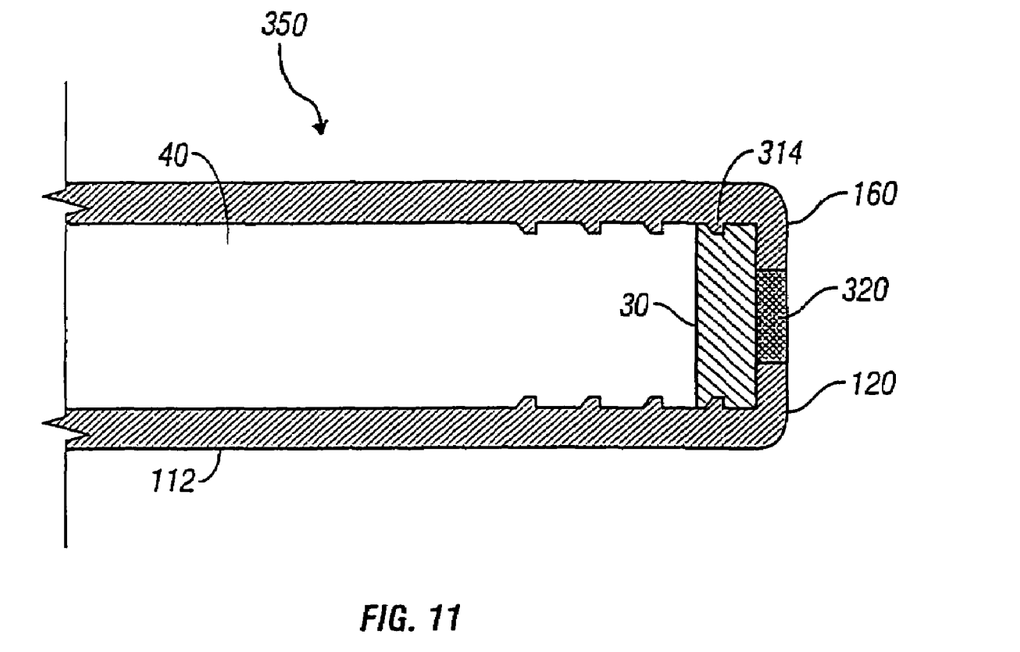
FIG. 11 is a cross-sectional side view of a portion of an implantable capsule according to a fourth embodiment of the invention.

FIG. 11 shows a portion of a fourth preferred embodiment of an osmotic delivery system 350. In this embodiment, the fluid uptake end 160 comprises the membrane material perforated disk 120 and a frit or sintered powdered metal structure 320. The frit 320 includes a plurality of capillaries having diameters between about 0.5 and 10 microns which allow fluid to pass therethrough and subsequently through the membrane material 30 into the interior of the capsule. In FIG. 11, the membrane material 30 is of sufficient length to include at least one rib or ridge 314. As can also be seen in FIG. 11, the frit 320 acts together with the ridges 314 to restrict the lateral movement of the membrane material 30 within the capsule 112. Thus, ridges 314 function in the same manner as the ridges 14 of the first embodiment. In this embodiment, the frit 320 is affixed, by welding, pressing, screwing or the like, to the membrane material perforated disk 120 of the capsule 112.

Figure 12:
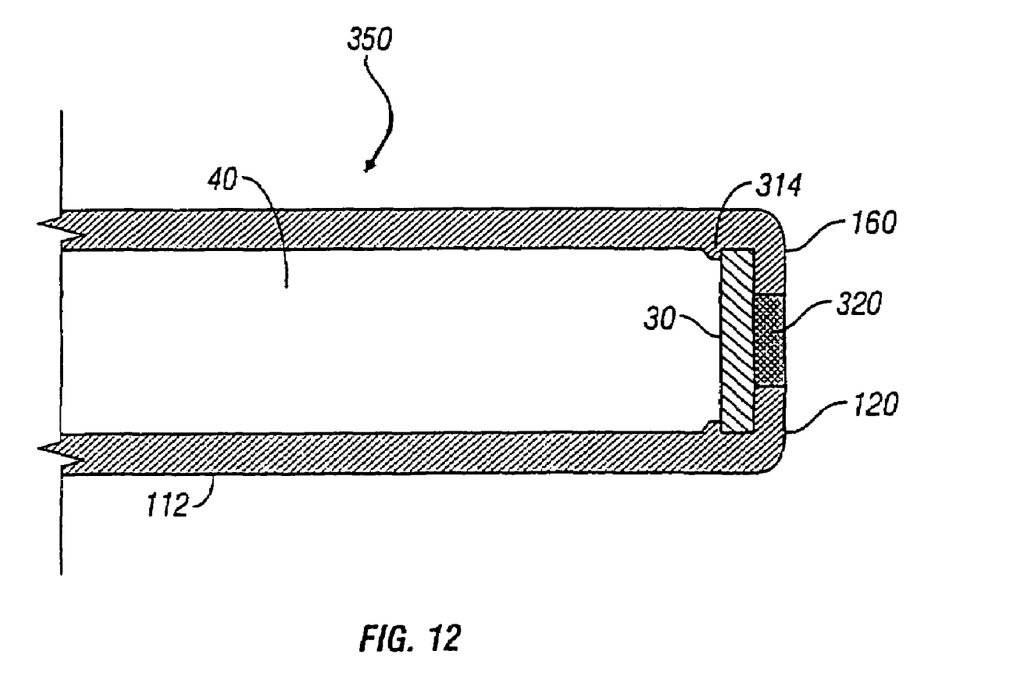
FIG. 12 is a cross-sectional side view of a portion of an implantable capsule according to a fifth embodiment of the invention.

FIG. 12 shows a portion of a fifth preferred embodiment of an osmotic delivery system 350. This embodiment is similar to the embodiment shown in FIG. 11 except that the membrane material 30 is located between the first rib or ridge 314 and the membrane material perforated disk 120. Movement of the membrane material 30 is restricted within the capsule 112 by both the ridge 314 and the membrane material perforated disk 120.

The membrane material can be prepared by casting, calendering, or extrusion. Casting comprises pouring the membrane material onto a flat surface. Calendering comprises forming a sheet of membrane material by pressing or rolling. Extrusion comprises pushing the membrane material through a die form to form a rod shape. Once the sheet or rod is prepared, the plug or disc shape is prepared by cutting or machining the sheet or rod. The cutting or machining can be accomplished, for example, by die-cutting or stamping the shape.

The devices of the invention are useful to deliver a wide variety of active agents. These agents include, but are not limited to, pharmacologically active peptides and proteins, genes and gene products, other gene therapy agents, and other small molecules. The polypeptides may include, but are not limited to, growth hormone, somatotropin analogues, somatomedin-C, Gonadotropic-releasing hormone, follicle-stimulating hormone, luteinizing hormone, LHRH, LHRH analogues such as leuprolide, nafarelin and goserelin, LHRH agonists and antagonists, growth hormone-releasing factor, calcitonin, colchicine, gonadotropins, such as chorionic gonadotropin, oxytocin, octreotide, somatotropin plus an amino acid, vasopressin, adrenocorticotrophic hormone, epidermal growth factor, prolactin, somatostatin, somatotropin plus a protein, cosyntropin, lypressin, polypeptides such as thyrotropin-releasing hormone, thyroid stimulation hormone, secretin, pancreozymin, enkephalin, glucagon, endocrine agents secreted internally and distributed by way of the bloodstream, and the like. Further agents that may be delivered include $\alpha_1$ antitrypsin, factor VIII, factor IX and other coagulation factors, insulin and other peptide hormones, adrenal cortical-stimulating hormone, thyroid-stimulating hormone and other pituitary hormones, interferon (for example, alpha, beta, gamma, and omega), erythropoietin, growth factors such as GCSF, GMCSF, insulin-like growth factor 1, tissue plasminogen activator, CD4, dDAVP, interleukin-1 receptor antagonist, tumor necrosis factor, pancreatic enzymes, lactase, cytokines, interleukin-1 receptor antagonist, interleukin-2, tumor necrosis factor receptor, tumor suppresser proteins, cytotoxic proteins, and recombinant antibodies and antibody fragments, and the like.

The above agents are useful for the treatment of a variety of conditions including, but not limited to, hemophilia and other blood disorders, growth disorders, diabetes, leukemia, hepatitis, renal failure, HIV infection, hereditary diseases such as cerebrosidase deficiency and adenosine deaminase deficiency, hypertension, septic shock, autoimmune diseases such as multiple sclerosis, Graves disease, systemic lupus erythematosus and rheumatoid arthritis, shock and wasting disorder, cystic fibrosis, lactose intolerance, Crohn's disease, inflammatory bowel disease, gastrointestinal and other cancers.

The active or beneficial agents may be anhydrous or aqueous solutions, suspensions or complexes with pharmaceutically acceptable vehicles or carriers such that a flowable formulation is produced that may be stored for long periods on the shelf or under refrigeration, as well as stored in an implanted delivery system. The formulations may include pharmaceutically acceptable carriers and additional inert ingredients. The active agents may be in various forms, such as uncharged molecules, components of molecular complexes or pharmacologically acceptable salts. Also, simple derivatives of the agents (such as prodrugs, ethers, esters, amides, etc.) which are easily hydrolyzed by body pH, enzymes, etc. can be employed.

It is to be understood that more than one active agent may be incorporated into the active agent formulation in a device of this invention and that the use of the term "agent" in no way excludes the use of two or more such agents. The dispensing devices of the invention find use, for example, in humans or other animals. The environment of use is a fluid environment and can comprise any subcutaneous position or body cavity, such as the peritoneum or uterus. Ultimate delivery may be systemic or targeted and may or may not be systemic delivery of the beneficial agent. A single dispensing device or several dispensing devices can be administered to a subject during a therapeutic program. The devices are designed to remain implanted during a predetermined administration period. If the devices are not removed following the administration, they may be designed to withstand the maximum osmotic pressure of the water-swellable agent or they may be designed with a bypass to release the pressure generated within the device.

The devices of the present invention are preferably rendered sterile prior to use, especially when such use is implantation. This may be accomplished by separately sterilizing each component, e.g., by gamma radiation, steam sterilization or sterile filtration, then aseptically assembling the final system. Alternatively, the devices may be assembled, then terminally sterilized using any appropriate method.

The assembly of the osmotic delivery device will be described below with reference to the embodiment of FIGS. 1–3, however, it should be understood that the embodiments of FIGS. 6–9 and 11 and 12 may be assembled in a similar manner.

According to a preferred embodiment, the capsule is assembled with the membrane retention flange 20 fixed to the capsule. The membrane material 30 is preferably inserted from the beneficial agent delivery end 70 of the capsule 12. The membrane material 30 is then slid through the length of the capsule 12, towards the direction of the fluid uptake end of the capsule 12 until it abuts a membrane material retention flange 20. The membrane material 30 may be inserted by, for example, compressed gas. In addition, as seen in FIG. 1, after the membrane material 30 has been fully inserted, the osmotic engine or osmotic agent may then be inserted into chamber 40 from the beneficial agent delivery end 70. Once the osmotic engine has been inserted, the piston 54 may then be inserted into the capsule. After insertion of the piston 54, the beneficial agent can be inserted into the first chamber 50 configured as a beneficial agent reservoir. Finally, the exit passageway or diffusion moderator is inserted into the beneficial agent delivery end 70.

Alternatively, the membrane retention flange 20 can be attached to the capsule after one or more of the membrane material 30, osmotic engine, piston 54, or beneficial agent has been inserted into the capsule 12.

If a screen, grate, or frit is present in opening 62, such screen, grate, or frit can be attached to capsule 12 before or after the membrane material 30 is placed in capsule 12.

Once all of the components of the osmotic delivery system 10 have been assembled, the beneficial agent delivery end 70 can be closed in a known manner, such as providing a cap with an exit passage 72. For example, the beneficial agent delivery end may be closed in the manner disclosed in commonly owned and assigned U.S. Pat. No. 5,728,396, issued to Peery et al., which is incorporated herein by reference.

Thus, the present invention provides a more consistent and predictable delivery rate of a beneficial agent by allowing for the use of cast, calendered or extruded membrane materials that are machined (i.e., die-cut, stamped or otherwise cut to shape), in which the permeability of the membrane materials are more homogeneous because they are produced on a highly controlled extrusion or machining line as compared to the part-to-part homogeneity of injection molded plugs.

According to other embodiments of the present invention, the delivery system may take different forms. For example, the piston may be replaced with a flexible member such as a diaphragm, partition, pad, flat sheet, spheroid, or rigid metal alloy, and may be made of any number of other materials. Furthermore, the osmotic device may function without the piston, having simply an interface between the osmotic agent/fluid additive and the beneficial agent or having the osmotic agent incorporated in the beneficial agent. In addition, the capsule of the present invention may be provided with a more rounded shape along its edges in order to make insertion of the capsule within the patient simpler.

The above-described exemplary embodiments are intended to be illustrative in all respects, rather than restrictive, of the present invention. Thus the present invention is capable of many variations and detailed implementation that can be derived from the description contained herein by a person skilled in the art. All such variations and modifications are considered to be within the scope and the spirit of the present invention as defined by the following claims.

We claim:

1. A delivery system for controlled delivery of a beneficial agent, the system comprising:
   an implantable capsule having a beneficial agent delivery end and a fluid uptake end, wherein the implantable capsule comprises one or a plurality of inwardly protruding ridges circumferentially arrayed near the fluid uptake end of the implantable capsule to securingly grip an outer surface of a membrane material;
   a beneficial agent reservoir positioned within the implantable capsule for delivery of the beneficial agent at a predetermined delivery rate;
   the membrane material received entirely within the fluid uptake end of the implantable capsule and providing a fluid permeable barrier between an interior and an exterior of the implantable capsule; and
   a membrane material-retaining means for preventing the membrane material from being ejected out of the fluid uptake end of the implantable capsule;
   wherein the membrane material-retaining means is positioned at the fluid uptake end of the implantable capsule and includes at least one opening for allowing passage of fluid.

2. The delivery system according to claim 1, wherein the membrane material-retaining means comprises a retention flange positioned along an outer periphery of the fluid uptake end.

3. The delivery system according to claim 2, wherein the retention flange and the implantable capsule are formed integrally.

4. The delivery system according to claim 2, wherein the retention flange is a separate member attached to the implantable capsule.

5. The delivery system according to claim 4, wherein the flange is attached to the implantable capsule by welding.

6. The delivery system according to claim 4, wherein the flange is attached to the implantable capsule by press fit.

7. The delivery system according to claim 4, wherein the flange is attached to the implantable capsule by screw means.

8. The delivery system according to claim 1, wherein the membrane material-retaining means comprises a screen or a grate.

9. The delivery system according to claim 1, wherein the membrane material-retaining means comprises a perforated disc.

10. The delivery system according to claim 1, wherein the membrane material-retaining means has a flat, rounded, or contoured surface on at least one surface thereof.

11. The delivery system according to claim 1, wherein the membrane material comprises a generally smooth, cylindrical shape.

12. The delivery system according to claim 1, wherein the membrane material has a diameter between about 0.040 inch and about 0.250 inch.

13. The delivery system according to claim 1, wherein the membrane material has a length or thickness between about 0.010 inch and about 0.350 inch.

14. The delivery system according to claim 1, wherein the membrane material is extruded, cast, or calendered.

15. The delivery system according to claim 14, wherein the membrane material is machined following extrusion, casting, or calendering.

16. The delivery system according to claim 1, wherein the membrane material is machined.

17. The delivery system according to claim 16, wherein the membrane material is die-cut.

18. The delivery system according to claim 1, wherein the one or a plurality of inward-protruding ridges are shaped to accommodate insertion of the membrane material, while preventing withdrawal of the membrane material from the implantable capsule.

19. The delivery system according to claim 1, further comprising an osmotic engine positioned between the beneficial agent delivery end and the membrane material.

20. The delivery system according to claim 19, further comprising a piston positioned between the beneficial agent delivery end and the osmotic engine for transmitting a pushing force created by the osmotic engine to the beneficial agent.

21. A delivery system for controlled delivery of a beneficial agent, the system comprising:
- an implantable capsule having a beneficial agent delivery end and a fluid uptake end, wherein the implantable capsule comprises one or a plurality of inwardly protruding ridges circumferentially arrayed near the fluid uptake end of the implantable capsule to securingly grip an outer surface of a membrane material;
- a beneficial agent reservoir positioned within the implantable capsule for delivery of the beneficial agent at a predetermined delivery rate;
- the membrane material received entirely within the fluid uptake end of the implantable capsule and providing a fluid permeable barrier between an interior and an exterior of the implantable capsule; and
- a membrane material-retaining means for preventing the membrane material from being ejected out of the fluid uptake end of the implantable capsule;
- wherein the membrane material-retaining means is positioned at the fluid uptake end of the implantable capsule and comprises a perforated disc.

22. A delivery system for controlled delivery of a beneficial agent, the system comprising:
- an implantable capsule having a beneficial agent delivery end and a fluid uptake end, wherein the implantable capsule comprises one or a plurality of inwardly protruding ridges circumferentially arrayed near the fluid uptake end of the implantable capsule to securingly grip an outer surface of a membrane material;
- a beneficial agent reservoir positioned within the implantable capsule for delivery of the beneficial agent at a predetermined delivery rate;
- the membrane material received entirely within the fluid uptake end of the implantable capsule and providing a fluid permeable barrier between an interior and an exterior of the implantable capsule, the membrane material comprising a generally smooth, cylindrical shape; and
- a membrane material-retaining means for preventing the membrane material from being ejected out of the fluid uptake end of the implantable capsule;
- wherein the membrane material-retaining means is positioned at the fluid uptake end of the implantable capsule and includes at least one opening for allowing passage of fluid.

23. A delivery system for controlled delivery of a beneficial agent, the system comprising:
- an implantable capsule having a beneficial agent delivery end and a fluid uptake end, wherein the implantable capsule comprises one or a plurality of inwardly protruding ridges circumferentially arrayed near the fluid uptake end of the implantable capsule to securingly grip an outer surface of a membrane material;
- a beneficial agent reservoir positioned within the implantable capsule for delivery of the beneficial agent at a predetermined delivery rate;
- the membrane material received entirely within the fluid uptake end of the implantable capsule and providing a fluid permeable barrier between an interior and an exterior of the implantable capsule, the membrane material comprising a generally smooth, cylindrical shape having a diameter between about 0.040 inch and about 0.250 inch; and
- a membrane material-retaining means for preventing the membrane material from being ejected out of the fluid uptake end of the implantable capsule;
- wherein the membrane material-retaining means is positioned at the fluid uptake end of the implantable capsule and includes at least one opening for allowing passage of fluid.

24. A delivery system for controlled delivery of a beneficial agent, the system comprising:
- an implantable capsule having a beneficial agent delivery end and a fluid uptake end, wherein the implantable capsule comprises one or a plurality of inwardly protruding ridges circumferentially arrayed near the fluid uptake end of the implantable capsule to securingly grip an outer surface of a membrane material;
- a beneficial agent reservoir positioned within the implantable capsule for delivery of the beneficial agent at a predetermined delivery rate;
- the membrane material received entirely within the fluid uptake end of the implantable capsule and providing a fluid permeable barrier between an interior and an exterior of the implantable capsule, the membrane material comprising a generally smooth, cylindrical shape having a length or thickness between about 0.010 inch and about 0.350 inch; and
- a membrane material-retaining means for preventing the membrane material from being ejected out of the fluid uptake end of the implantable capsule;
- wherein the membrane material-retaining means is positioned at the fluid uptake end of the implantable capsule and includes at least one opening for allowing passage of fluid.

25. The delivery system according to claim 1, wherein the membrane material-retaining means comprises a porous disc.

* * * * *